United States Patent [19]

Reith et al.

[11] Patent Number: 4,754,083

[45] Date of Patent: Jun. 28, 1988

[54] PARA SELECTIVITY IN CATALYZED DISUBSTITUTIONS OF MONOSUBSTITUTED BENZENES CONTAINING META-DIRECTING SUBSTITUENTS

[75] Inventors: Robert A. Reith, Glen Ellyn; Glen R. Hoff, Naperville, both of Ill.

[73] Assignee: Amoco Corporation, Chicago, Ill.

[21] Appl. No.: 855,348

[22] Filed: Apr. 24, 1986

[51] Int. Cl.⁴ .............................................. C07C 79/10
[52] U.S. Cl. .................................... 568/932; 568/939
[58] Field of Search ............... 568/939, 340, 932, 937, 568/938

[56] References Cited

U.S. PATENT DOCUMENTS

| | | | |
|---|---|---|---|
| 2,109,873 | 3/1938 | Wilhelm | 568/939 |
| 4,107,220 | 8/1978 | Owsley et al. | 568/937 |
| 4,112,006 | 9/1978 | Schubert et al. | 568/940 |
| 4,418,230 | 11/1983 | Bakke et al. | 568/939 X |
| 4,426,543 | 1/1984 | Schumacher et al. | 568/940 |
| 4,467,126 | 8/1984 | Zinnen | 568/940 X |
| 4,551,568 | 11/1985 | Sato et al. | 568/939 |
| 4,642,396 | 2/1987 | Can et al. | 568/934 |

*Primary Examiner*—Teddy S. Gron
*Assistant Examiner*—Susan Wolffe
*Attorney, Agent, or Firm*—Reed F. Riley; William H. Magidson; Ralph C. Medhurst

[57] ABSTRACT

Para selectivity in the conversion of a monosubstituted benzene containing a meta-directing group to disubstituted benzenes can be substantially enhanced by carrying out the reaction in the gas phase with an inorganic or organic substitution agent in the presence of a catalyst composition comprising a crystalline molecular sieve material. In particular, nitrobenzene can be converted using nitrogen dioxide in the gas phase to a product containing an augmented proportion of para-dinitrobenzene using a wide range of catalyst compositions comprising both synthetic and naturally occurring crystalline molecular sieve materials such as ferrierites, X-type zeolites, Y-type zeolites, silicalite, framework-modified silicalites, ZSM aluminosilicates, AMS-1B borosilicates, and AlPO₄ types.

10 Claims, No Drawings

PARA SELECTIVITY IN CATALYZED DISUBSTITUTIONS OF MONOSUBSTITUTED BENZENES CONTAINING META-DIRECTING SUBSTITUENTS

BACKGROUND OF THE INVENTION

This invention relates to improved para positional selectivity in the catalyzed conversion of monosubstituted benzenes containing meta-directing substituents to disubstituted benzenes and, more particularly, to a process for improving para selectivity in the conversion of a monosubstituted benzene such as nitrobenzene to a disubstituted benzene such as dinitrobenzene comprising contacting under conversion conditions, for example, the nitrobenzene in the gas phase with an inorganic or organic substitution agent such as nitrogen dioxide in the presence of a catalyst composition comprising a crystalline molecular sieve material.

In U.S. Pat. No. 4,415,744 to Monsanto, aromatics including unsubstituted, monosubstituted, and disubstituted compounds are described which are catalytically nitrated in the vapor phase with nitrogen dioxide over a sulfur trioxide-treated alumina-silica-metal oxide combination, $(Al_2O_3)_a(SiO_2)_b(M_2/O)_c$. Combinations include aluminosilicates such as synthetic and naturally-occurring zeolites. An essential step in making this nitration promoting catalyst is its activation with sulfur trioxide. European Patent Application No. 0092372 to Sumitomo teaches the gas-phase nitration of benzene by nitrogen dioxide over an acidic mixed oxide containing not less than two metallic oxides and containing at least one component selected from the group $WO_3$, $MoO_3$ and $TiO_2$. The catalysts are said to avoid production of by-products such as dinitrobenzene. Another European Patent Application, No. 0053031 to Monsanto, teaches the vapor-phase nitration of aromatic compounds "susceptible of existing in the vapor phase at temperatures less than 190° C." in the presence of molecular sieve catalysts. Reaction temperature is limited to between 80° and 190° C. and ferrierite, Zeolite X, and Zeolite Y are named as useful catalysts. The use of a phosphorus-vanadium-oxygen complex to nitrate aromatics in the gas phase using nitrogen dioxide is taught by Monsanto in U.S. Pat. No. 4,347,389. In European Patent Application No. 0093522, acidic solid surfaces including those of zeolites are used to catalyze the vapor-phase nitration of organic compounds, primarily aliphatics, with a combination of nitrogen dioxide and hydrogen peroxide. The nitration of benzene or toluene using gasified nitric acid over acid catalysts of the zeolite type, preferably montmorillonite, is taught in British Pat. No. 2000141. This patent describes enhanced para selectivity in the nitration of toluene, which is ortho-para not meta directing, compared to a solution nitration process using a mixture of nitric and sulfuric acids. European Patent Application No. 0017560 describes the gas-phase nitration of lower-than-$C_5$ paraffins using nitrogen peroxide, nitric acid, or compounds containing a transferable nitro or nitrosyl group. The use of nitric acid as a gas-phase nitrating agent, this time for toluene, is described in U.S. Pat. No. 4,112,006. In the U.S. Pat. No. 4,112,006 the process is carried out in the presence of a carrier substance based on silica and/or alumina which may additionally contain a minor quantity of a different inorganic oxide such as magnesia, the carrier being impregnated by a high boiling inorganic acid such as phosphoric acid or sulfuric acid and, optionally, a salt of such an acid, e.g., iron or aluminum sulfate or phosphate. U.S. Pat. No. 4,107,220 teaches controlling the ortho-para isomer distribution in the products during the catalyzed gas-phase nitration of chlorobenzene with an oxide of nitrogen such as nitrogen dioxide. The molecular sieve catalysts taught by the U.S. Pat. No. 4,107,220 are crystalline synthetic zeolites having a pore size from about 5 to about 10 Å and include Zeolon 300 and 900, AW-500 sieve, 13× molecular sieve, etc. Finally, McKee and Wilhelm in *Industrial and Engineering Chemistry* 28, 6, 662–7 (1936) teach the catalyzed vapor-phase nitration of benzene and toluene over silica gel using a nitrogen oxide.

Zeolitic materials, both natural and synthetic, are known to have catalytic capabilities for many hydrocarbon conversion processes. Such materials typically are ordered porous crystalline aluminosilicates having a definite structure with cavities interconnected by channels. The cavities and channels throughout the crystalline material generally are uniform in size allowing selective separation of hydrocarbons. Consequently, these materials, in many instances, are known in the art as "molecular sieves" and are used, in addition to selective adsorptive processes, for certain catalytic properties. The catalytic properties of these materials are affected, to some extent, by the size of the molecules which selectively penetrate the crystal structure, presumably to contact active catalytic sites within the ordered structure of these materials.

Generally, the term "molecular sieve" includes a wide variety of both natural and synthetic positive-ion-containing crystalline zeolite materials. They generally are characterized as crystalline aluminosilicates which comprise networks of $SiO_4$ and $AlO_4$ tetrahedra in which silicon and aluminum atoms are cross-linked by sharing of oxygen atoms. The negative framework charge resulting from substitution of an aluminum atom for a silicon atom is balanced by positive ions, for example, alkali-metal or alkaline-earth-metal cations, ammonium ions, or hydrogen ions.

Prior art developments have resulted in the formation of many synthetic zeolitic crystalline materials. Crystalline aluminosilicates are the most prevalent and, as described in the patent literature and in the published journals, are designated by letters or other convenient symbols. Examples of these materials are Zeolite A (U.S. Pat. No. 2,882,243), Zeolite X (U.S. Pat. No. 2,882,244), Zeolite Y (U.S. Pat. No. 3,130,007), Zeolite ZSM-4 (U.S. Pat. No. 3,578,723), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), Zeolite NU-1 (U.S. Pat. No. 4,060,590), and others. In addition, although boron is not considered a replacement for aluminum or silicon in a zeolite composition, a borosilicate sieve is described in U.S. Pat. Nos. 4,268,420 and 4,269,813.

One of the problems in the reaction chemistry of monosubstituted aromatics is the directing effect of the substituent already present on the ring on the entering position of a second substituent. A substituent on a benzene ring can be classified according to its ability to direct a second substituent to one of the three different positions on the monosubstituted ring. For example, alkyl and halo substituents direct the second group largely to the 2 and 4 positions forming ortho and para derivatives. Nitro, carboxylic acid, and sulfonic acid substituents on the other hand direct the second substituent largely to the 3 position forming meta derivatives. The directing influence can be quite strong; for example, in the conventional liquid-phase nitration of nitrobenzene a mixture of dinitrobenzenes is produced which contains about 93 percent of the meta isomer.

Now it has been found that by carrying out a substitution reaction on a monosubstituted benzene containing a meta-directing group in the gas phase over a crystalline molecular sieve the meta-directing influence of the substituent can be substantially reduced and a high proportion of the unfavored para isomer formed at good conversion levels.

SUMMARY OF THE INVENTION

Described herein is a process to improve the para selectivity in the conversion of a monosubstituted benzene containing a meta-directing group to a disubstituted benzene wherein the monosubstituted benzene is combined under conversion conditions in the gas phase with an organic or inorganic substitution agent in the presence of a catalyst composition comprising a crystalline molecular sieve. In particular, nitrobenzene can be converted in the gas phase to dinitrobenzene with nitrogen dioxide under conversion conditions in the presence of a catalyst composition comprising an inorganic crystalline molecular sieve material.

DETAILED DESCRIPTION OF THE INVENTION

In carrying out the process of the instant invention the monosubstituted benzene is reacted in the gas phase with an organic or inorganic substitution agent capable of adding a second substituent to the monosubstituted benzene in the presence of a catalyst composition comprising any of a wide number of naturally occurring and synthetic crystalline molecular sieves, preferably those which have pore sizes large enough to accommodate the monosubstituted benzene under conversion conditions. Useful sieves are naturally occurring and synthetic crystalline inorganic molecular sieves or clays having molecular size discriminating properties such as mordenites and their cation-exchanged variants, chabazites and their cation-exchanged variants, A-, X-, and Y-type sieves and their cation-exchanged variants, AMS-1B borosilicate sieves, ZSM-4, 5, 11, 12, etc. aluminosilicate zeolites and their cation-exchanged variants, silicalite, crystalline silicas in which a small portion of framework silicon has been replaced by one or more of chromium, zinc, gallium, cadmium and the like, ELZ-$\Omega$ sieves and the like, Beta-type sieves, H-ferrierites and their metal-exchanged variants, H-montmorillonites and their metal-exchanged variants, and AlPO$_4$ type sieves, particularly those having pore sizes greater than about 5 Å, measured under conversion conditions. More preferred are H- and metal-exchanged mordenites, H-ferrierites, and X-type sieves and most preferred are H-ferrierite sieves with Si/Al atom ratios greater than about 8 and less than about 30 and NaX sieves.

The molecular sieves useful for carrying out this invention are generally high surface area materials, preferably greater than about 100 sq. meters per gram and more preferably, greater than about 200 sq. meters per gram. Many of the sieves useful herein have surface areas greater than about 300 sq. meters per gram.

The effective pore size of a sieve can be measured using standard adsorption techniques and hydrocarbonaceous compounds of known minimum kinetic diameters. See Breck "Zeolite Molecular Sieves" (1974) John Wiley and Sons, especially Chapter 8, and Anderson et al. J. Catalysis 58, 114 (1979).

The crystalline molecular sieve can be admixed with or incorporated within various active or inactive binders or matrix materials depending upon the sieve and the intended process of employing the instant catalyst compositions. Well-known materials include silica, silica-alumina, alumina, magnesia, titania, zirconia, alumina sols, hydrated aluminas, clays such as kaolin, or other binders well known in the art. Typically, the molecular sieve is incorporated within a matrix material by blending with a sol of the matrix material and gelling the resulting mixture. Also, solid particles of the molecular sieve and matrix material can be physically admixed. Typically, such catalyst compositions can be pelletized or extruded into useful shapes. The molecular sieve content can vary anywhere from a few up to 100 wt.% of the total composition. Catalytic compositions can contain about 0.1 wt.% to about 100 wt.% crystalline molecular sieve material and preferably contain about 10 wt.% to about 100 wt.% of such material and most preferably contain about 20 wt.% to about 100 wt.% of such material. Many of the sieves useful in this invention are most effective used without matrixing although commercial practice may dictate matrixing the sieve even if selectivity and conversion are adversely affected. Of course, a matrixing agent which reacts adversely with either the substitution agent or the monosubstituted benzene is not preferred.

Catalyst compositions of this invention can be impregnated with a small amount of a magnesium or phosphorus compound or treated with a silylating agent such as triphenylsilyl chloride according to procedures well known in the art for added para selectivity. Conversion may, however, be reduced by such impregnation or treatment.

Monosubstituted benzenes suitable for use in the instant invention include those with substituents having a meta-directing effect. Preferably, the monosubstituted benzene used is nitrobenzene.

The substitution agent useful in substituting the monosubstituted benzene can be an organic or inorganic agent and includes such compounds as alkylating and halogenating agents. More preferably, it is nitrogen dioxide which, when reacted with nitrobenzene, produces a product comprising dinitrobenzenes containing an enhanced amount of the para isomer. Because of the well-known temperature and pressure dependent dimerization of nitrogen dioxide, this term as used herein embraces both monomer and dimer.

For the reactions described herein, no distinction is made between the terms vapor-phase and gas-phase reactions, and the term gas-phase reaction is used to cover reactions of all the monosubstituted benzenes described.

Various reactor types can be employed in carrying out the instant invention. For example, the substitution reaction can be carried out in a fixed catalyst bed or fluidized catalyst bed configuration with appropriate changes in, for example, the physical form of the catalyst composition as is well known to those skilled in the art.

In effecting the catalyzed reaction of the monosubstituted benzene with the substitution agent, conversion conditions include a temperature between about 150° C. and about 400° C., more preferably about 250° to about 350° C., a pressure between about 1 atmosphere and about 150 atmospheres, more preferably between about 1 atmosphere and 30 atmospheres, utilizing a feed weight hourly space velocity between about 0.1 and about 100 hrs$^{-1}$, more preferably between about 1 and about 50 hrs$^{-1}$, and a molar feed ratio of substitution agent to monosubstituted benzene between about 0.5 and about 50, more preferably between about 1 and about 15. If the substitution reaction is very exothermic, for example, in the nitration of nitrobenzene, the substitution agent, nitrogen dioxide, can be diluted by an inert gaseous diluent, for example, nitrogen. Dilution and other methods of reaction heat removal are well known to those skilled in the art and can readily be applied to the teachings of this invention.

The reaction product consisting of substitution products and perhaps unreacted monosubstituted benzene and some of the substitution agent may be separated by any suitable means such as fractionation, etc.

The following Examples will serve to illustrate certain specific embodiments of the hereindisclosed invention. These Examples should not, however, be construed as limiting the scope of the novel invention described herein as there are many variations which may be made thereon without departing from the spirit of the disclosed invention, as may be understood by one skilled in the art.

EXAMPLES

General Experimental Procedure

The catalyzed gas-phase nitration runs were carried out in a continuous manner on bench scale equipment in two ways; one way converted nitrobenzene (NB) to dinitrobenzene (DNB) in a fixed bed reactor and the other in a fluidized bed reactor. Both are described below. The reaction product was analyzed using a gas chromatograph equipped with a 10 ft. by ⅛ inch s.s. column packed with 10% SP-2100 on 80/100 mesh Supelcoport®, and the GC results are expressed in weight percent of a component for the conversions, yields, and isomer percents.

Identification of Commercial Molecular Sieves and Clays Used

HY sieve is Grace Co. hydrogen-exchanged zeolite Y which is a sodium aluminum silicate with 7.4 Angstrom (12 ring) apertures leading to a 13 Angstrom cavity. Zeolons 400 H, 500 H and 900 H are Norton Company hydrogen-exchanged sieves having $SiO_2/Al_2O_3$ ratios of 10:1, 5:1 and 10-13:1 respectively. They have effective pore diameters of 3.5, 4.3 and 8-9 Angstroms respectively. AW 500 H is a Linde Co. acid washed, hydrogen-exchanged Y-type sieve in 20% clay binder. It contains about 65% silica and 22.7% alumina with a BET surface of 500 m$^2$/g and a pore diameter of about 5 Angstroms. ELZ-$\Omega$-5 is a Linde Co. sieve having a $SiO_2/Al_2O_3$ ratio of 7.7 and a $Na_2O/Al_2O_3$ ratio of 0.6. It has a free aperture of 7.5 Angstroms (12 ring) and a surface area of 240 m$^2$/g. H-ELZ-L is a Linde Co. hydrogen-exchanged sieve having a silica/alumina ratio of about 3.1, a BET surface area of about 372 m$^2$/2, and a pore size of about 8-10 Angstroms (12 ring). Silicalite S-115 is a Linde Co. sieve of >99% silica having a free aperture (zig zag channels) of 5.4 Angstroms and (straight channels) 5.75 Angstroms by 5.15 Angstroms.

Linde 13X sieve is a hydrated sodium aluminum silicate which has a pore diameter of about 10 Angstroms and is supplied pure or in a 20 weight percent inert clay binder. It can be exchanged with hydrogen ion or other cations such as calcium and ammonium ion. LZ-Y-52 and LZ-Y-20 are both Linde sieves having a pore size of 8-10 Angstroms. The former sieve is about 63.8% silica, 22.9% alumina and 13.0% sodium oxide. The LZ-Y-20 sieve is a Y sieve containing 75.9% silica and 23.1% alumina which has a BET surface area of about 600 m$^2$/g. Linde 4A sieve is a hydrated sodium aluminum silicate supplied generally in 20% inert clay binder which has pore diameter of about 4 Angstroms.

Volclay 325, a naturally occurring montmorillonite, was supplied by American Colloid Co., contained about 58% silica, 18% alumina, 2.5% iron (III) oxide, 2.5% magnesium oxide, 1.5% sodium and potassium as sodium oxide, 5.6% water and smaller percentages of other oxides. It was hydrogen exchanged before use.

Fluidized Bed Procedure

A nitrogen/nitrogen dioxide gaseous mixture (mol ratio about 2/1 to 9/1) was led into a vertical preheater which was a short, narrow diameter heated pyrex tube filled with quartz pieces wherein the mixture was combined with vaporized aromatic compound supplied through a calibrated syringe or piston pump. The effluent from the preheater which was held at 250° C. was conducted into a one inch o.d. vertical pyrex tubular reactor heated to 300° C., the conical bottom of which contained additional quartz which supported a charge of 10 ml. (3-9 grams) of catalyst. Gas flow rates were fast enough to at least partially fluidize the 40/50 mesh catalyst composition samples used. Reactant and products were condensed downstream in a water-cooled primary receiver and two backup traps cooled with dry ice. In runs using this procedure, the reaction pressure was near ambient, mol ratio nitrogen dioxide to aromatic compound ranged from about 1.5 to 9, and mol percent aromatic compound in the gas phase between about 2 and 6. Catalyst contact time was between about 0.25 to 1 sec. unless otherwise noted. Each run was two hours in length after a short lining out period. The data in Tables I-IV represents the average of samples collected during the first hour and the second hour.

Fixed Bed Procedure

The fixed bed unit was similar to the fluidized bed unit. However, reactor temperature was generally 315° C. and the catalyst composition charge was supported on a layer of glass wool and glass beads and occupied roughly the center section (longitudinally) of the pyrex glass reactor tube. In these runs the catalyst composition was pretreated briefly with either nitrobenzene or with a nitrogen/nitrogen dioxide mixture (greater than 9/1), after which the aromatic compound was added to the gas stream. The nitrogen dioxide-to-aromatic ratio in the reactor was kept between about 3/1 and 10/1. Catalyst compositions employed were either commercially available materials, generally used as ⅛ inch by 1/16 inch extrudates, or, if prepared in-house, were generally first prepared as powders, pressed into a disk and then crushed and screened to a 0.5 to 2.5 mm size suitable for the reactor. Runs were one hour in length which followed a generally one hour lining-out period. The data in Table V represents the material collected over the one hour run.

EXAMPLE 1

A 37.02 g portion of sodium hydroxide was dissolved in 400 ml of distilled water and 207.09 g of tetrapropyl ammonium bromide added and also dissolved. Then a 42.00 g portion of sodium aluminate was added and dissolved followed by 1077 g of AS-40 Ludox. Sufficient additional distilled water was added to make the total volume of solution 1800 ml. The mixture was stirred for 15 minutes and heated under autogenous pressure for six days at 149° C. in an autoclave fitted with a Teflon ® liner. The result was separated by filtration and washed by slurrying three times in distilled water at 82° C. The solid was calcined at 527° C. for four hours. A 436 g portion of the solid was exchanged three times at 82° C. with a solution made from 436 g of ammonium nitrate and 2500 ml of distilled water. The exchanged material was then dried three times by slurrying with distilled water at 82° C. and dried at 121° C. It was calcined at 527° C. for four hours before use to give the hydrogen forms. The product contained 5 ppm sodium, 42.9% silicon, 2.01% aluminum, and was about 83% crystalline by XRD as H-ZSM-5.

EXAMPLE 2

A 100 g portion of sodium hydroxide was dissolved in 1150 g of distilled water. A 26.8 g portion of sodium aluminate was then added and dissolved. A 109.2 g amount of piperidine was added followed by 481.6 g of HS-40 Ludox. The resulting mass was stirred on a hot plate for 10 min, put into a Teflon ®-lined autoclave and heated under autogeneous pressure for five days at 143° C. The result was filtered, washed three times with hot water, dried at 121° C. overnight, and calcined four hours at 527° C. The calcined material was exchanged three times at 82° C. with a solution made from 176.4 g of ammonium nitrate dissolved in 2500 ml of distilled water. The exchanged sieve was washed by reslurrying in distilled water at 82° C., dried overnight at 120° C., and calcined for four hours at 527° C. The sieve contained 87% silica, 6.18% alumina, 444 ppm sodium, and had a minimum crystallinity of 85% by XRD as H-ferrierite.

EXAMPLE 3

A 179 ml portion of ethylenediamine was dissolved in 700 g of distilled water and 93 g of $H_3BO_3$ was added. After the $H_3BO_3$ was dissolved, 200 g of isopropylalcohol was added and a 500 g portion of Nalco 2372 silica stirred into the resulting solution. This result was poured into a Parr reactor and digested at 165° C. while stirring at 300 RPM. The sieve was filtered, washed with three liters of distilled water, and dried. It was then calcined at 543° C. for 12 hours. The sieve contained 1.98% boron, 0.057% aluminum, 229 ppm iron, 55 ppm sodium, and 41.4% silicon. Using XRD this boron containing ferrierite was shown to exhibit medium crystallinity. The sieve was exchanged using several portions of ammonium acetate solution, washed, and dried at about 100° C. A solution of $Al(NO_3)_3.9H_2O$ was prepared from 1.81 g of the nitrate and 44 ml of dionized water. This solution was poured onto 12.2 g of the sieve and the water evaporated at about 100° C. The resulting 12.56 g of material were calcined at 538° C. for about 16 hours giving a material 11.66 g in weight which was about 1% by weight in aluminum.

EXAMPLE 4

A 360 g portion of N-Brand sodium silicate, 672 ml of distilled water and 4 g of sodium aluminate were mixed and the pH of the resulting solution adjusted to below 10 by adding 35 g of concentrated sulfuric acid. A second solution was made up by dissolving 44 g of tetrabutylphosphonium chloride in 608 g of distilled water and the two solutions mixed in a large beaker and stirred with heating for 1½ hr. The result was heated in a closed autoclave for three days at 149° C. The results was filtered, washed three times by reslurrying, dried, and calcined at 121° C. and 572° C., respectively. Analysis by XRD showed the sieve to be 74% crystalline as ZSM-11. An 81 g portion of the sieve was exchanged three times with hot ammonium nitrate solution. It was then washed three times and dried overnight at 121° C. The product contained 5.6 ppm sodium, 90.77% silica, 1.15% alumina, and 6.50% volatiles.

EXAMPLE 5

A 121.5 g portion of sodium hydroxide was dissolved in 933 g of distilled water with stirring. A 40.5 g portion of sodium aluminate was dissolved in the result while heating gently with stirring. A 100 g portion of benzyltrimethylammonium chloride was added as a 50 wt.% solution in water while agitating. Finally, 723 g of Ludox AS-40 were added and enough additional distilled water to make a total volume of 1800 ml. After heating and stirring this mixture for 15 min the result was transferred to a Teflon ®-lined, sealed autoclave and heated at 100° C. for one day. To this material in the autoclave after cooling, 25.00 g of potassium hydroxide were added, the autoclave resealed, and the autoclaving continued for 14 days. The product was separated by filtering, then washed, dried overnight at 121° C., and calcined at 572° C. for four hours. The product shows essentially the Erionite structure with a very small percentage of material having Offretite structure present. This product was exchanged three times with a solution made from 71.09 g of ammonium nitrate dissolved in 2000 ml of water and washed well with hot distilled water by reslurrying three times. It was dried at 121° C. and calcined at 572° C.

EXAMPLE 6

To a 500 ml. amount of distilled water was added and dissolved a 6.46 g portion of aluminum acetate. Then a 1.70 g portion of gallium oxide was dissolved in the solution. The template, 24.5 g of 1,9-diaminononane were then added and dissolved. After the pH was raised to 13.1 with 9.81 g of sodium hydroxide, the silica source, Ludox AS-40 (150.87 grams) was added with stirring. The mixture was digested at 163° C. in a stainless steel autoclave for eight days. The product was filtered, washed with distilled water, dried for four hours at 165° C., and then calcined at 530° C. for 12 hours. The resulting material was exchanged twice with $NH_4OAc$ solutions and dried at 165° C. for 12 hours. The crystalline product contained 1.28% aluminum, 2.43% gallium, 38.6% silicon, and had a surface of 320 sq. meters per gram and a micropore volume of 0.13 cc/g.

EXAMPLE 7

A 12.50 g amount of sodium hydroxide was dissolved in 1150 ml of distilled water. To this solution 20.10 g of sodium aluminate were added and dissolved with stirring and heating. A 91.33 g portion of piperidine was then added and dissolved. To this solution was added 481.60 g of HS-40 Ludox and enough distilled water to make the total volume 1800 ml. The reuslt was autoclaved for five days at 149° C., separated by filtration, washed, dried overnight at 121° C., and calcined at 572° C. for four hours. The sieve contains 0.24% sodium, 88.7% silica, 4.65% alumina, and 5.60% volatiles. By XRD it was 88% crystalline as a ferrierite structure.

EXAMPLE 8

A 12.50 g portion of sodium hydroxide was dissolved in 1150 ml of distilled water with stirring. A 20.1 g portion of sodium aluminate was dissolved in the solution with stirring and heating. Then, 91.3 g of piperdine followed by 481.6 g of HS-40 Ludox were added. The result was autoclaved at 149° C. for six days. After removing from the autoclave the solution was filtered and the solid washed three times with 2500 ml of distilled water and dried at 121° C. The resulting solid was determined to be 93% crystalline by XRD as a ferrierite structure. After calcining at 538° C. for four hours, 794 g of the material was exchanged three times with a solution containing 794 g of ammonium nitrate in six liters of water at 82° C. The resulting solid was washed three times with four liters of distilled water at 82° C. and dried at 250° C. overnight. Analysis shows 43.2% silicon, 3.05% aluminum, 5.3 ppm sodium, and 2.76% volatiles.

EXAMPLE 9

A 34.01 g portion of sodium hydroxide, 44.05 g of sodium aluminate.$3H_2O$, and 80.58 g of 2,4-pentanedione were dissolved in 1000 g of distilled water with mixing. A 515.01 g amount of Ludox HS-40 silica sol was added. The mixture was stirred briefly, sealed in an autoclave, and digested three days at 165° C. The sieve was filtered, washed with eight liters of water, and dried four hours at 165° C. The dried material was calcined at 540° C. for 12 hours. A 200.86 g portion of the calcined solid was exchanged twice with a solution containing 401.01 g of ammonium acetate dissolved in 3000 ml of water, washed with four liters of water, and dried at 165° C. The resulting solid was calcined at 540° C. for 12 hours. The sieve contains 4.2% aluminum and is 83% crystalline by XRD as a ferrierite structure.

EXAMPLE 10

A 10.0 g portion of sodium hydroxide was dissolved in 1150 ml of distilled water with heating and stirring. A 26.8 g amount of sodium aluminate was added followed by 109.2 of piperidine. Then a 481.6 g amount of Ludox HS-40 was added with heating and stirring and the mixture autoclaved for six days at 149° C. The autoclave was decanted, the solid filtered, and washed three times with 2500 ml of distilled water. The resulting sieve was dried at 81° C. and calcined 12 hours at 572° C. On analysis, it contained 41.6% silicon, 3.14% aluminum, 0.8 ppm sodium, and is 83% crystalline by XRD as a ferrierite structure.

EXAMPLE 11

A 250 g portion of the sieve of Example 8 was mixed with 12.5 g of Sterotex ® and pelletized. The pellets were calcined for two hours at 288° C., two hours at 399° C., and four hours at 538° C.

EXAMPLE 12

To 502 g of distilled water was added with stirring 24.26 g of 1,8-diaminooctane, 10.14 g of aluminum acetate, and 13.222 g of NaOH. Then a 150.00 g portion of Ludox AS-40 was added and the mixture stirred for about 10 min. The pH at this point was 12.9. The mixture was transferred to an autoclave and autoclaved six days at 152° C. The contents of the autoclave were filtered, dried at about 100° C., and calcined at about 540° C. The resulting sieve was exchanged twice with ammonium acetate solution, dried at about 100°, and recalcined. The solid is 88% crystalline by XRD as a ferrierite structure, contained 2.86% aluminum, 40.3% silicon, and had a Si/Al ratio of 13.05.

EXAMPLE 13

A 304.1 g portion of chlorhydrol (50 wt. % solution in water) silica supplied by the Reheis Chemical Co. was placed in a breaker and 2270 ml of water added with stirring. A 400 g portion of Volclay 325, supplied by the American Colloid Co., was added and the liquid agitated with warming. The pH of the solution was maintained at 3.7–4.3 by adding 3% ammonia solution. It was then heated at 70° C. for one hour, filtered, and dried at 100° C. The expanded clay was calcined at 500° C. for two hours. By XRD the pillared Bentonite had a d spacing of 16.6 Å.

EXAMPLE 14

Various sieves were employed using the technique set forth under Fluidized Bed Procedure above for the nitration of nitrobenzene. The results are set forth in Tables I and II below.

TABLE I

Fluidized Bed Nitration of Nitrobenzene
Unsupported Catalysts

| Preparative Example No. | Catalyst Designation | NB Conversion % | DNB Yield % | Isomer Distribution, %[3] | | |
|---|---|---|---|---|---|---|
| | | | | Ortho | Meta | Para |
| | 12/40 quartz[1] | ~0 | <0.1 | T[6] | T[6] | T[6] |
| | HY[2] | 88 | 48.1 | 6 | 81 | 13 |
| | Zeolon 900H[4] | 58 | 18.5 | 6 | 71 | 24 |
| 1 | H—ZSM-5 | 40 | 22.9 | 4 | 89 | 8 |
| | Zeolon 400H[4] | 8 | 6.3 | 8 | 70 | 23 |
| 2 | H—Ferrierite | 10 | 9.6 | 7 | 50 | 44 |
| | AW-500H[5] | 12 | 6.4 | 14 | 70 | 17 |
| | Zeolon 500H[4] | 8 | 5.4 | 12 | 72 | 16 |
| | H—Montmorillonite[7] | 17 | 9.5 | 11 | 73 | 16 |
| | AlPO$_4$-5[8] | 9 | 0.7 | 22 | 62 | 16 |
| 3 | Boroferrierite (1% Al impregnated) | 2 | 3 | 12 | 76 | 13 |
| | ELZ-Ω-5[5] | 15 | 13 | 11 | 56 | 33 |
| | H—ELZ-L[5] | 42 | 27.6 | 12 | 68 | 20 |
| | H—Beta[9] | 74 | 43 | 8 | 68 | 25 |
| 4 | H—ZSM-11 | 42 | 29.5 | 5 | 83 | 12 |
| 5 | H—Erionite | 15 | 5.8 | 9 | 68 | 23 |
| 6 | Gallosilicate | 11 | 6.9 | 6 | 82 | 13 |
| | Silicalite S-115[5] | 13 | 4.8 | 6 | 82 | 13 |

[1]Quartz tubing ground and sieved to the designated mesh size.
[2]Z-14 U.S. supplied by Grace Co., acid exchanged.
[3]Solution nitration of nitrobenzene with a mixture of nitric and sulfuric acids produces a mixture of 6% ortho, 93% meta, and 1% para dinitrobenzene.
[4]Supplied by the Norton Company.
[5]Supplied by the Linde Division of Union Carbide Corp.
[6]Trace.
[7]Volclay 325 supplied by the American Colloid Co.
[8]U.S. Pat. No. 4,310,440, Example No. 3.
[9]U.S. Pat. Re 28,341, Ex. 6. Ammonium exchanged and calcined.

TABLE II

Fluidized Bed Nitration of Nitrobenzene
Unsupported Catalysts

| Preparative Example No. | Catalyst Designation | NB Conversion % | DNB Yield % | Isomer Distribution, % | | |
|---|---|---|---|---|---|---|
| | | | | Ortho | Meta | Para |
| | Mg-Mor- | 21 | 7 | 6 | 66 | 28 |

TABLE II-continued

Fluidized Bed Nitration of Nitrobenzene
Unsupported Catalysts

| Preparative Example No. | Catalyst Designation | NB Conversion % | DNB Yield % | Isomer Distribution, % | | |
|---|---|---|---|---|---|---|
| | | | | Ortho | Meta | Para |
| | denite[1] | | | | | |
| | 13X Pure[2] | 10 | 5.1 | 14 | 40 | 47 |
| | 13X Pure[2,3] | 17 | 4.3 | 13 | 36 | 51 |
| | 13X 20%[2] Binder | 12 | 6.6 | 13 | 39 | 48 |
| | Ca—X[4] | <8 | 8.6 | 25 | 58 | 17 |
| | H—Y low Na[5] | 89 | 48.1 | 6 | 81 | 13 |
| 7 | H—Ferrierite (2400 ppm Na+) | 17 | 10 | 5 | 47 | 48 |
| 8 | H—Ferrierite (0.5 ppm Na+) | 10 | 8.7 | 6 | 49 | 45 |
| 12 | H—Ferrierite | 9 | 9.3 | 12 | 59 | 30 |
| 13 | Pillared Bentonite | 10 | 9.4 | 7 | 76 | 17 |

[1]Zeolon 900H exchanged with magnesium acetate.
[2]Supplied by the Linde Div. of Union Carbide Corp.
[3]Temperature was 325° C. rather than 300° C. and mol percent NB in gas phase was 2.
[4]13X sieve exchanged with a calcium salt.
[5]Z-14 U.S. supplied by Grace Co.

EXAMPLE 15

Various sieves were supported and employed using the technique set forth under Fluidized Bed Procedure above for the nitration of nitrobenzene. The results are set forth in Table III below.

TABLE III

Fluidized Bed Nitration of Nitrobenzene
Supported Catalysts

| Preparative Example No. | Catalyst Designation | NB Conversion % | DNB Yield % | Isomer Distribution, % | | |
|---|---|---|---|---|---|---|
| | | | | Ortho | Meta | Para |
| | Quartz[1] | 0 | <0.1 | T[4] | T[4] | T[4] |
| | γ-alumina[2] | 0 | <0.2 | T[4] | T[4] | T[4] |
| 9 | H—Ferrierite (unsupported) | 29 | 17.4 | 5 | 81 | 15 |
| | H—Ferrierite[3] (40% on silica) | 13 | 10.8 | 6 | 82 | 13 |
| | H—Ferrierite[3] (40% on γ-Al$_2$O$_3$) | 12 | 7.4 | 2 | 94 | 5 |
| 1 | H-ZSM-5 (unsupported) | 43 | 22.9 | 4 | 89 | 8 |
| | H-ZSM-5[3] (40% on γ-Al$_2$O$_3$) | 11 | 18.1 | 1 | 94 | 5 |
| | HAMS-1B[3] (40% on γ-Al$_2$O$_3$) | 20 | 13 | 3 | 89 | 9 |

[1]Quartz tubing ground and sieved to the designated mesh.
[2]Supplied by the American Cyanamid Co., Aeroform PHF 5A blanks extrudate.
[3]Made by gel method.
[4]Trace.

EXAMPLE 16

Several ferrierite sieves with differing Si/Al atomic ratios were employed using the technique set forth under Fluidized Bed Procedure above for the nitration of nitrobenzene. The results are set forth in Table IV below.

TABLE IV

Fluidized Bed Nitration of Nitrobenzene Over H—Ferrierite
Effect of Si/Al Ratio Change

| Ex. No. | Wt. % Al | Si/Al Atomic Ratio | NB Conversion % | DNB Yield % | Isomer Distribution, % | | |
|---|---|---|---|---|---|---|---|
| | | | | | Ortho | Meta | Para |
| 10 | 3.1 | 12.8 | 21 | 11.2 | 6 | 49 | 45 |
| 10 | 3.2 | 11.9 | 9 | 6.3 | 7 | 47 | 47 |
| 2 | 3.3 | 12.0 | ~10 | 9.6 | 7 | 50 | 44 |
| 10 | 3.6 | 10.4 | 13 | 11.6 | 10 | 59 | 32 |
| 9 | 4.2 | 9.0 | 29 | 17.4 | 5 | 81 | 15 |

EXAMPLE 17

Various sieves were employed as set forth in the Fixed Bed Procedure above and used for the nitration of nitrobenzene. The results are set forth in Table V below.

TABLE V

Fixed Bed Nitration of Nitrobenzene

| Catalyst Designation | NB Conversion % | DNB Yield % | Isomer Distribution, % | | |
|---|---|---|---|---|---|
| | | | Ortho | Meta | Para |
| 13X extrudate[1] ⅛" | 23.7 | 7.1 | 12 | 45 | 43 |
| 13X on Al$_2$O$_3$[1] | 18.8 | 12.7 | 10 | 50 | 41 |
| 13X on Kaolin[1] | 24.8 | 12.1 | 10 | 50 | 40 |
| 13X[1] | 18 | 7.6 | 11 | 42 | 47 |
| NH$_4$X[2] | 25.7 | 12 | 11 | 61 | 27 |
| HX[3] | 21 | 13 | 13 | 62 | 26 |
| LZ-Y-52[1] | 40.4 | 12.7 | 6 | 83 | 11 |
| LZ-Y-20[1] | 72.1 | 49.3 | 6 | 80 | 14 |
| H—Ferrierite[4] | 44 | 18.5 | 3 | 40 | 57 |
| 4A[1] | 4.5 | 1.3 | 14 | 56 | 30 |
| AW-500[1] | 7.4 | 5 | 12 | 75 | 14 |
| AW-500[1,5] | 8.7 | 8.4 | 12 | 74 | 15 |

[1]Supplied by the Linde Division of Union Carbide Corporation.
[2]13X exchanged with an ammonium salt solution.
[3]13X exchanged with an ammonium salt solution and calcined at 300° C.
[4]Example 11.
[5]Reaction temp. of 326° C.

What is claimed is:

1. A process for nitrating nitrobenzene to form primarily dinitrobenzenes which comprises contacting nitrobenzene and nitrogen dioxide in the gas phase under conversion conditions in the presence of a catalyst composition comprising an inorganic crystalline molecular sieve material, pillared Bentonite or a hydrogen exchanged montmorillonite clay.

2. The process of claim 1 wherein said sieve has a pore size large enough to accommodate said nitrobenzene under conversion conditions.

3. The process of claim 2 wherein said sieve is substantially the hydrogen form of a ferrierite.

4. The process of claim 2 wherein said sieve is a X-type sieve.

5. The process of claim 3 wherein the Si/Al ratio of said ferrierite is between about 8 to 1 and about 30 to 1.

6. The process of claim 4 wherein said sieve is a NaX sieve.

7. The process of claim 5 wherein said catalyst composition comprises said sieve incorporated in an inorganic matrix.

8. The process of claim 6 wherein said catalyst composition comprises said sieve incorporated in an inorganic matrix.

9. The process of claim 5 wherein said catalyst composition comprises from about 10 to about 100 wt. % of said sieve incorporated into a silica, silica-alumina, or kaolin matrix.

10. The process of claim 6 wherein said catalyst composition comprises from about 10 to about 100 wt. % of said sieve incorporated in a silica, silica-alumina, alumina or kaolin matrix.

* * * * *